(12) United States Patent
Schmidt et al.

(10) Patent No.: US 6,893,774 B2
(45) Date of Patent: May 17, 2005

(54) FLUOROALKYLPHOSPHATE SALTS, AND PROCESS FOR THE PREPARATION OF THESE SUBSTANCES

(75) Inventors: Michael Schmidt, Seeheim-Jugenheim (DE); Andreas Kuhner, Darmstadt (DE); Nikolai Ignatyev, Duisburg (DE); Peter Sartori, Utting (DE)

(73) Assignee: Merck Patent GmbH, Darmstadt (DE)

( * ) Notice: Subject to any disclaimer, the term of this patent is extended or adjusted under 35 U.S.C. 154(b) by 411 days.

(21) Appl. No.: 10/080,515

(22) Filed: Feb. 25, 2002

(65) Prior Publication Data

US 2002/0122979 A1 Sep. 5, 2002

(30) Foreign Application Priority Data

Feb. 24, 2001 (DE) .......................... 101 09 032

(51) Int. Cl.$^7$ ..................... H01M 6/016; H01M 10/04; H01G 9/022; C07F 9/028
(52) U.S. Cl. ................. 429/189; 429/199; 429/307; 429/323; 252/62.2; 361/505; 568/16

(58) Field of Search ................. 429/189, 199, 429/307, 323; 252/62.2; 361/505; 568/16

(56) References Cited

U.S. PATENT DOCUMENTS

2002/0015884 A1 * 2/2002 Schmidt et al. ............. 429/188

OTHER PUBLICATIONS

Fild, M. et al. ("Methylene Compounds of nonmetals. V. Methylenediphosphorous halides", Z. Anorg. Allg. Chem. (1987), 555, 109–17).*

* cited by examiner

Primary Examiner—Susy Tsang-Foster
(74) Attorney, Agent, or Firm—Millen, White, Zelano, Branigan, P.C.

(57) ABSTRACT

Fluoroalkylphosphate salts of Formula I, described herein, are suitable for use, alone or in mixtures with, e.g., other salts, in electrolytes, primary batteries, secondary batteries, capacitors, supercapacitors or galvanic cells.

44 Claims, No Drawings

FLUOROALKYLPHOSPHATE SALTS, AND PROCESS FOR THE PREPARATION OF THESE SUBSTANCES

The present invention relates to fluoroalkylphosphate salts and to a process for their preparation. The present invention furthermore relates to mixtures which comprise the fluoroalkylphosphate salts according to the invention, and to the use of these salts or these mixtures in electrolytes, primary batteries, secondary batteries, capacitors, supercapacitors or galvanic cells.

The spread of portable electronic equipment, such as, for example, laptop and palmtop computers, mobile telephones or video cameras, and thus also the demand for lightweight and high-performance batteries, has increased dramatically worldwide in recent years.

In view of this suddenly increased demand for batteries and the associated ecological problems, the development of rechargeable batteries with a long service life is of constantly increasing importance.

Rechargeable lithium ion batteries have been commercially available since the early nineties. Most of these batteries work with lithium hexafluorophosphate as conductive salt. However, this lithium salt is an extremely hydrolysis-sensitive compound with low thermal stability, and consequently the corresponding lithium batteries, owing to these properties of the salt, can only be produced by very complex and thus also very expensive processes.

In addition, the hydrolysis-sensitive compound reduces the service life and the performance of these lithium batteries and also impairs their use under extreme conditions, such as, for example, high temperatures.

For these reasons, lithium perfluoroalkylfluorophosphates, which have better chemical and electrochemical stabilities and high discharge efficiency compared with conventional $LiPF_6$, have been developed for lithium batteries as conductive salts in electrolytes of high-energy lithium batteries. The high hydrolysis stability of lithium perfluoroalkylfluorophosphates makes them interesting as powerful lithium batteries in electric vehicles (M. Schmidt, U. Heider, A. Kühner, R. Oesten, M. Jungnitz, N. Ignat'ev, P. Sartori. J. of Power Sources (accepted), WO 98/15562 (Merck KGaA), P 100 08 955.0 (Merck KGaA), N. Ignat'ev and P. Sartori, J. of Fluorine Chem., 101 (2000), p. 203–207).

The disadvantage of these substances lies in their high molecular weight and the resultant low content of $Li^+$ cations per weight unit of conductive salt.

SUMMARY OF THE INVENTION

An object of the present invention is therefore to provide stable conductive salts having a higher content of cations per weight unit of conductive salt.

A further object of the invention is to extend or improve the service life and the performance of primary and secondary batteries, capacitors, supercapacitors and/or galvanic cells.

Upon further study of the specification and appended claims, further objects and advantages of this invention will become apparent to those skilled in the art.

These objects are achieved by the provision of novel fluoroalkylphosphate salts of the general formula (I)

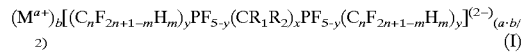

in which $M^{a+}$ is a monovalent, divalent or trivalent cation, a=1, 2 or 3, b=2 for a=1, b=2 for a=3, b=1 for a=2 and in each case $1 \leq n \leq 8$, $0 \leq m \leq 2$ for n=1 or 2, $0 \leq m \leq 4$ for $3 \leq n \leq 8$, $1 \leq x \leq 12$, $0 \leq y \leq 2$, where $R_1$ and $R_2$ are identical or different and are selected from the group consisting of fluorine, hydrogen, or alkyl, fluoroalkyl and perfluoroalkyl substituents each having 1 to 8, preferably 1 to 3 carbon atoms, and where the substituents $(C_nF_{2n+1-m}H_m)$ are in each case identical or different.

Preference is given to fluoroalkylphosphate salts of the general formula (I) according to the invention in which the cation $M^{a+}$ is an alkali metal cation, preferably a lithium, sodium or potassium cation, particularly preferably a lithium cation, or a magnesium or aluminium cation.

Preference is furthermore also given to fluoroalkylphosphate salts of the general formula (I) in which the cation $M^{a+}$ is an organic cation, preferably a nitrosyl cation, a nitryl cation or a cation of the general formula $[N(R^7)_4]^+$, $[P(R^7)_4]^+$, $[P(N(R^7)_2)_4]^+$ or $[C(N(R^7)_2)_3]^+$, where the radicals $R^7$ are in each case identical or different and are H, alkyl ($C_{1-10}$) or A, where any H atoms in the alkyl chain may be substituted by fluorine or an aromatic radical, optionally containing heteroatoms, preferably N, O and/or S, or a cycloalkyl radical, preferably having 5–6 members, optionally containing heteroatoms, preferably N, O and/or S, and/or C atoms in the alkyl chain may be replaced by heteroatoms, preferably oxygen.

A is an aromatic or cycloaliphatic radical, which in each case may optionally contain heteroatoms, preferably selected from N, O, and S. A may be any aromatic, heteroaromatic or cycloaliphatic radicals known to the person skilled in the art and suitable for the preparation of $[N(R^7)_4]^+$, $[P(R^7)_4]^+$, $[P(N(R^7)_2)_4]^+$ or $[C(N(R^7)_2)_3]^+$ cations.

A is preferably in each case a 5- or 6-membered aromatic radical, optionally containing nitrogen and/or sulfur and/or oxygen atoms, or a cycloalkyl radical, preferably having 5 or 6 members, particularly preferably a phenyl or pyridine radical.

In a further preferred embodiment of the present invention, the cation $M^{a+}$ is a heteroaromatic cation selected from the group consisting of the heteroaromatic cations of the general formulae (II) to (IX):

(II)
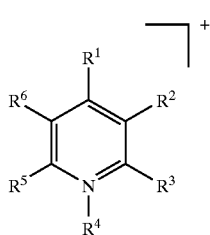

(III)
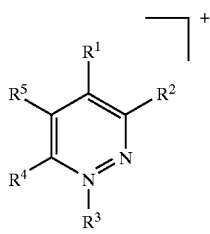

(IV)
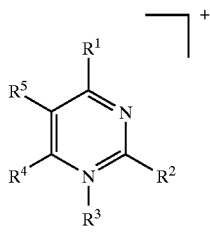

(V)
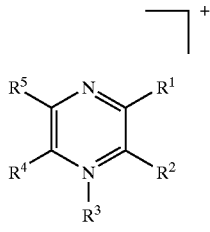

(VI)
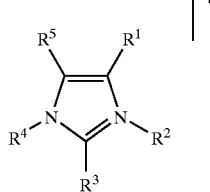

(VII)
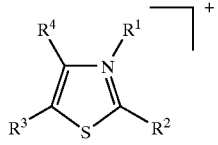

(VIII)
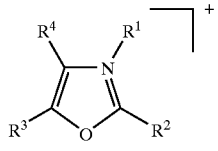

(IX)
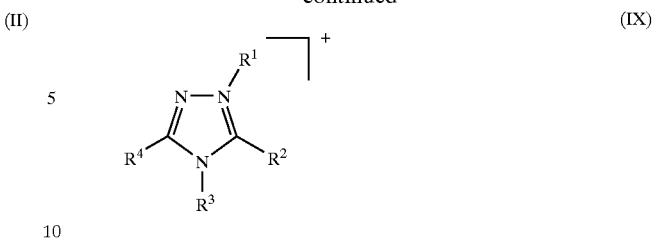

The radicals $R^1$ to $R^6$, which may in each case be identical or different, are an H radical, a halogen radical, preferably a fluorine radical, or a $C_{1-8}$-alkyl radical, which may optionally be substituted by the substituents F, Cl, $N(C_rF_{(2r+1-s)}H_s)_2$, $O(C_rF_{(2r+1-s)}H_s)$, $SO_2(C_rF_{(2r+1-s)}H_s)$ or $C_rF_{(2r+1-s)}H_s$, in which $1 \leq r \leq 6$ and $0 \leq s \leq 13$, and $2r+1-s$ is $\geq 0$.

It is also possible for one or more pair of adjacent radicals $R^1$ to $R^6$ together to be a $C_{1-8}$-alkylene radical, which may optionally be substituted by the substituents F, Cl, $N(C_rF_{(2r+1-s)}H_s)_2$, $O(C_rF_{(2r+1-s)}H_s)$, $SO_2(C_rF_{(2r+1-s)}H_s)$ or $C_rF_{(2r+1-s)}H_s$, in which $1 \leq r \leq 6$, $0 \leq s \leq 2r+1$, and $2r+1-s$ is $\geq 0$.

It should be noted that the radicals $R^1$ to $R^6$ in the heteroaromatic cations of the general formulae (II) to (IX) cannot be halogens if the radicals $R^1$ to $R^6$ are bonded directly to nitrogen.

Preference is likewise given to fluoroalkylphosphate salts of the general formula (I) in which $1 \leq n \leq 6$, preferably $1 \leq n \leq 3$.

Preference is also given to fluoroalkylphosphate salts of the general formula (I) in which $1 \leq x \leq 8$, preferably $1 \leq x \leq 4$.

Particular preference is given to fluoroalkylphosphate salts of the general formula (I) in which m=0.

Very particular preference is given to fluoroalkylphosphate salts of the general formula (I) in which y=2.

Very particular preference is also given to the fluoroalkylphosphate salts of the general formula (I) according to the invention in which $R_1$ and $R_2$ are fluorine.

Particular preference is given to the fluoroalkylphosphate salts of the general formula (I):

$$(Li^+)_2[(C_2F_5)_2PF_3(CF_2)_2PF_3(C_2F_5)_2]^{(2-)}$$

and $$(N(C_2H_5)_4^+)_2[(C_2F_5)_2PF_3(CF_2)_2PF_3(C_2F_5)_2]^{(2-)}$$

The salts of the general formula (I) according to the invention can be employed, both in pure form and in the form of their mixtures, as conductive salts in electrolytes, primary and secondary batteries, capacitors, supercapacitors and/or galvanic cells. The salts according to the invention are preferably used in pure form as conductive salts since in this way particularly good reproducibility of the electrochemical properties can be ensured. However, it is likewise possible to use the salts according to the invention as conductive salts in the form of a mixture with further salts known to the person skilled in the art.

They can be used in proportions of between 1 and 99% in combination with other conductive salts used in electrochemical cells. Suitable are, for example, conductive salts selected from the group consisting of $LiPF_6$, $LiBF_4$, $LiClO_4$, $LiAsF_6$, $LiCF_3SO_3$, $LiN(CF_3SO_2)_2$, $LiN(CF_3CF_2SO_2)_2$, $LiC(CF_3SO_2)_3$ or lithium fluoroalkylphosphates of the general formula Li[PF$_{(6-c)}$(C$_d$F$_{2d+1}$)], where $1 \leq c \leq 5$ and $1 \leq d \leq 8$, and LiN[SO$_2$(C$_e$F$_{2e+1}$)]$_2$, LiCSO$_2$(C$_e$F$_{2e+1}$)]$_3$ and Li[SO$_3$(C$_e$F$_{2e+1}$)], where $2 \leq e \leq 8$, and mixtures thereof.

The salts of the formula (I) and mixtures thereof can likewise be used in electrolytes for electrochemical cells.

The electrolytes may also comprise organic isocyanates (DE 199 44 603, this citation being incorporated herein by way of reference and thus being regarded as part of the disclosure) in order to reduce the water content.

The invention furthermore relates to a process for the preparation of fluoro-alkylphosphate salts according to the invention. In this process, at least one fluoro-α,ω-bis[(fluoroalkyl)fluorophosphorano)alkane is reacted with at least one fluoride salt of the general formula (X)

$(M^{a+})[F^-]_a$      (X)

in which ($M^{a+}$) and a are as defined above, in solution to give a fluoroalkyl-phosphate salt of the general formula (I) according to the invention, and the latter is, where appropriate, purified and/or isolated by conventional methods.

In a preferred embodiment of the process according to the invention, the fluoro-α,ω-bis[(fluoroalkyl)fluorophosphorano]alkanes employed are at least one compound of the general formula (XI)

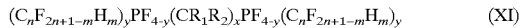

(C$_n$F$_{2n+1-m}$H$_m$)$_y$PF$_{4-y}$(CR$_1$R$_2$)$_x$PF$_{4-y}$(C$_n$F$_{2n+1-m}$H$_m$)$_y$      (XI)

in which
$1 \leq n \leq 8$, $0 \leq m \leq 2$ for n=1 or 2, $0 \leq m \leq 4$ for $3 \leq n \leq 8$, $1 \leq x \leq 12$, $0 \leq y \leq 2$,
where R$_1$ and R$_2$ are identical or different and are selected from the group consisting of fluorine, hydrogen, or alkyl, fluoroalkyl and perfluoroalkyl substituents each having 1 to 8, preferably 1 to 3 carbon atoms, and where the substituents (C$_n$F$_{2n+1-m}$H$_m$) are in each case identical or different.

Of the processes according to the invention, preference is given to those in which the compound of the general formula (X) is employed in an excess of up to 10 fold, preferably up to 5 fold, particularly preferably up to 2 fold, based on the amount of fluoro-α,ωbis[(fluoroalkyl)fluorophosphorano]alkane(s). Compounds of the general formula (X) are very particularly preferably employed in twice the equimolar amount based on the fluoro-α,ω-bis[(fluoro-alkyl)fluorophosphorano]alkane employed.

In the processes according to the invention, the reaction with the fluoride salt of the general formula (X) is preferably carried out at a temperature of from −35 to +80° C., preferably from −20 to +50° C., particularly from 10 to 25° C.

Suitable solvents for the above-mentioned processes are organic carbonates, preferably ethylene carbonate, propylene carbonate, butylene carbonate, dimethyl carbonate, diethyl carbonate, ethyl methyl carbonate or methyl propyl carbonate, organic esters, preferably methyl formate, ethyl formate, methyl acetate, ethyl acetate, methyl propionate, ethyl propionate, methyl butyrate, ethyl butyrate or γ-butyrolactone, organic ethers, preferably diethyl ether, dimethoxyethane or diethoxyethane, organic amides, preferably dimethyl-formamide or dimethylacetamide, sulfur-containing solvents, preferably dimethyl sulfoxide, dimethyl sulfide, diethyl sulfide or propane sulfone, aprotic solvents, preferably acetonitrile, acrylonitrile, propionitrile or acetone, or at least partially fluorinated derivatives of the above-mentioned solvents, or mixtures of at least two of these solvents and/or fluorinated derivatives of these solvents.

The fluoroalkylphosphate salts of the general formula (I) according to the invention are also suitable for use in solid electrolytes. For the purposes of the present invention, the term solid electrolytes is taken to mean both polymer electrolytes, which usually comprise an optionally crosslinked polymer and a conductive salt, and also gel electrolytes, which, besides an optionally cross-linked polymer and a conductive salt, usually additionally comprise at least one solvent.

The present invention therefore furthermore relates to a mixture comprising
a) at least one fluoroalkylphosphate salt of the general formula (I)
and
b) at least one polymer.

For the purposes of the present invention, the term mixture covers pure mixtures of components a) and b), mixtures in which the salt of component a) is included in the polymer of component b), and mixtures in which chemical and/or physical bonds exist between the salt of component a) and the polymer of component b).

In a preferred embodiment of the present invention, the mixture according to the invention comprises from 5 to 90% by weight of component a) and from 95 to 5% by weight of component b), particularly preferably from 10 to 80% by weight of component a) and from 90 to 20% by weight of component b). The stated weight ratios are in each case based on the sum of components a) and b).

As component b), the mixture according to the invention preferably comprises a homopolymer or copolymer of acrylonitrile, vinylidene difluoride, methyl (meth)acrylate, tetrahydrofuran, ethylene oxide, siloxane, phosphazene or a mixture of at least two of the above-mentioned homopolymers and/or copolymers.

Component b) is particularly preferably a homopolymer or copolymer of vinylidene difluoride, acrylonitrile, methyl (meth)acrylate or tetrahydrofuran, very particularly preferably a homopolymer or copolymer of vinylidene difluoride.

These homopolymers and copolymers of vinylidene fluoride are marketed under the name Kynare® and Kynarflex® by Atofina Chemicals, Inc., and under the name Solef® by Solvay.

The polymers used in accordance with the invention may also be at least partially crosslinked. The crosslinking can be carried out using known crosslinking agents by conventional methods known to the person skilled in the art.

Besides the fluoroalkylphosphate salts of the general formula (I) and the polymers, the mixture according to the invention may additionally comprise a solvent or a solvent mixture of two or more solvents.

Preferred solvents are organic carbonates, preferably ethylene carbonate, propylene carbonate, butylene carbonate, dimethyl carbonate, diethyl carbonate, ethyl methyl carbonate or methyl propyl carbonate, organic esters, preferably methyl formate, ethyl formate, methyl acetate, ethyl acetate, methyl propionate, ethyl propionate, methyl butyrate, ethyl butyrate or γ-butyrolactone, organic ethers, preferably diethyl ether, dimethoxyethane or diethoxyethane, organic amides, preferably dimethylformamide or dimethylacetamide, sulfur-containing solvents, preferably dimethyl sulfoxide, dimethyl sulfide, diethyl sulfide or propane sulfone, aprotic solvents, preferably acetonitrile, acrylonitrile or acetone, or at least partially fluorinated derivatives of the above-mentioned solvents, or mixtures of at least two of these solvents and/or fluorinated derivatives of these solvents.

The present invention furthermore relates to the use of at least one fluoroalkyl-phosphate salt according to the invention or of a mixture according to the invention in electrolytes, primary batteries, secondary batteries, capacitors, supercapacitors and/or galvanic cells, if desired also in combination with further, known conductive salts and/or additives.

The invention furthermore relates to electrolytes, primary and secondary batteries, capacitors, supercapacitors and galvanic cells which contain at least one fluoroalkylphosphate salt of the general formula (I) according to the invention or a mixture according to the invention and, if desired, further conductive salts and/or additives. Further conductive salts and additives are known to the person skilled in the art, for example from Doron Auerbach, Nonaqueous Electrochemistry, Marc Dekker Inc., New York 1999; D. Linden, Handbook of Batteries, Second Edition, McGraw-Hill Inc., New York 1995, and G. Mamantov and A. I. Popov, Chemistry of Nonaqueous Solutions, Current Progress, VCH Verlagsgeselischaft, Weinheim 1994. They are hereby incorporated by way of reference and are regarded as part of the disclosure.

Electrolytes according to the invention preferably have a concentration of the fluoroalkylphosphate salt(s) according to the invention of from 0.01 to 3 mol/l, preferably from 0.01 to 2 mol/l, particularly preferably from 0.1 to 1.5 mol/l.

As solvents for the salts according to the invention, the electrolytes preferably comprise organic carbonates, preferably ethylene carbonate, propylene carbonate, butylene carbonate, dimethyl carbonate, diethyl carbonate, ethyl methyl carbonate or methyl propyl carbonate, organic esters, preferably methyl formate, ethyl formate, methyl acetate, ethyl acetate, methyl propionate, ethyl propionate, methyl butyrate, ethyl butyrate or γ-butyrolactone, organic ethers, preferably diethyl ether, dimethoxyethane or diethoxyethane, organic amides, preferably dimethylformamide or dimethylacetamide, sulfur-containing solvents, preferably dimethyl sulfoxide, dimethyl sulfide, diethyl sulfide or propane sulfone, aprotic solvents, preferably acetonitrile, acrylonitrile or acetone, or at least partially fluorinated derivatives of the above-mentioned solvents, or mixtures of at least two of these solvents and/or fluorinated derivatives of these solvents.

The fluoroalkylphosphate salts according to the invention and the mixtures according to the invention have the advantage that they exhibit absolutely no or virtually no signs of decomposition over a very long period in the presence of water and have good to very good solubility in most solvents or solvent mixtures.

Furthermore, they have high thermal stability and high chemical stability both in the solid state and in the dissolved state. Thus, the salts and mixtures according to the invention are stable, for example to strong oxidants, such as, for example, to highly oxidising electrode materials, such as, for example, $LiMn_2O_4$, $LiNiO_2$ or $LiCoO_2$.

These properties enable electrolytes, batteries, capacitors, supercapacitors and galvanic cells which contain these conductive salts to be employed under extreme conditions, such as, for example, at high temperatures, without their service life and performance being impaired by these conditions.

Furthermore, the corresponding batteries, capacitors, supercapacitors and galvanic cells are distinguished by very good voltage constancy, unrestricted ability to function over many charging and discharging cycles, and by low production costs.

The use of the fluoroalkylphosphate salts according to the invention or the mixtures according to the invention in large batteries, as used, for example, in electric road vehicles or hybrid road vehicles, is likewise very advantageous since, in the case of damage to the batteries, such as, for example, in the case of an accident, including in the case of contact with water, for example through atmospheric moisture or extinguishing water, toxic and highly caustic hydrogen fluoride is not formed.

The compounds according to the invention and mixtures thereof can be used in electrolytes for electrochemical cells. They can be employed as conductive salts or additives. They can likewise be used in proportions of between 1 and 99% in combination with other conductive salts used in electrochemical cells. Suitable are, for example, conductive salts selected from the group consisting of $LiPF_6$, $LiBF_4$, $LiClO_4$, $LiAsF_6$, $LiCF_3SO_3$, $LiN(CF_3SO_2)_2$, $LiN(CF_3CF_2SO_2)_2$ and $LiC(CF_3SO_2)_3$ and mixtures thereof.

The electrolytes may also comprise organic isocyanates (DE 199 44 603) for reducing the water content.

It is also possible for compounds of the general formula

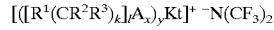

where
Kt is N, P, As, Sb, S or Se
A is N, P, P(O), O, S, S(O), $SO_2$, As, As(O), Sb or Sb(O)
$R^1$, $R^2$ and $R^3$
are identical or different
and are H, halogen, substituted and/or unsubstituted alkyl $C_nH_{2n+1}$, substituted and/or unsubstituted alkenyl having 2–18 carbon atoms and one or more double bonds, substituted and/or unsubstituted alkynyl having 2–18 carbon atoms and one or more triple bonds, substituted and/or unsubstituted cycloalkyl $C_mH_{2m-1}$, mono- or polysubstituted and/or unsubstituted phenyl, or substituted and/or unsubstituted heteroaryl,
A may be included in $R^1$, $R^2$ and/or $R^3$ in various positions,
Kt may be included in a cyclic or heterocyclic ring,
the groups bonded to Kt may be identical or different,
where
n is 1–18
m is 3–7
k is 0 or 1–6
l is 1 or 2 in the case where x=1 and 1 in the case where x=0
x is 0 or 1
y is 1–4
to be present (DE 19941566 and U.S. Ser. No. 09/654,519, filed Sep. 1, 2000). The process for the preparation of the compounds is characterised in that an alkali metal salt of the general formula

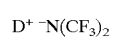

where $D^+$ is selected from the group consisting of the alkali metals, is reacted, in a polar organic solvent, with a salt of the general formula

where
Kt, A, $R^1$, $R^2$, $R^3$, k, l, x and y are as defined above, and
$^-E$ is $F^-$, $Cl^-$, $Br^-$, $I^-$, $BF_4^-$, $ClO_4^-$, $AsF_6^-$, $SbF_6^-$ or $PF_6^-$.
The compounds according to the invention may also be present in electrolytes comprising compounds of the formula

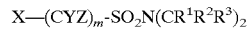

where

X is H, F, Cl, $C_nF_{2n+1}$, $C_nF_{2n-1}$ or $(SO_2)_kN(CR^1R^2R^3)_2$

Y is H, F or Cl

Z is H, F or Cl $R^1$, $R^2$ and $R^3$ are H and/or alkyl, fluoroalkyl or cycloalkyl m is 0–9 and, if X=H, m≠0 n is 1–9 k is 0 if m=0 and k=1 if m=1–9, prepared by reacting partially or perfluorinated alkylsulfonyl fluorides with dimethylamine in organic solvents (DE 199 466 73 and U.S. Ser. No. 09/671,619, filed Sep. 28, 2000).

It is also possible to use electrolytes comprising complex salts of the general formula (DE 199 51 804 and U.S. Ser. No. 09/698,478, filed Oct. 30, 2000)

$$M^{x+}[EZ]_{x/y}{}^{y-}$$

in which:

x and y are 1, 2, 3, 4, 5 or 6

$M^{x+}$ is a metal ion

E is a Lewis acid selected from the group consisting of $BR^1R^2R^3$, $AlR^1R^2R^3$, $PR^1R^2R^3R^4R^5$, $AsR^1R^2R^3R^4R^5$ and $VR^1R^2R^3R^4R^5$, $R^1$ to $R^5$ are identical or different, are optionally bonded directly to one another by a single or double bond, and each, individually or together, are a halogen (F, Cl or Br), an alkyl or alkoxy radical ($C_1$ to $C_8$), which may be partially or fully substituted by F, Cl or Br, an aromatic ring, optionally bonded via oxygen, from the group consisting of phenyl, naphthyl, anthracenyl and phenanthrenyl, which may be unsubstituted or mono- to hexasubstituted by alkyl ($C_1$ to $C_8$) or F, Cl or Br, an aromatic heterocyclic ring, optionally bonded via oxygen, from the group consisting of pyridyl, pyrazyl and pyrimidyl, which may be unsubstituted or mono- to tetrasubstituted by alkyl ($C_1$ to $C_8$) or F, Cl or Br, and Z is $OR^6$, $NR^6R^7$, $CR^6R^7R^8$, $OSO_2R^6$, $N(SO_2R^6)(SO_2R^7)$, $C(SO_2R^6)(SO_2R^7)(SO_2R^8)$ or $OCOR^6$, where $R^6$ to $R^8$ are identical or different, are optionally bonded directly to one another by a single or double bond and are each, individually or together, hydrogen or as defined for $R^1$ to $R^5$.

These complex salts can be prepared by reacting a corresponding boron or phosphorus Lewis acid/solvent adduct with a lithium or tetraalkylammonium imide, methanide or triflate.

Borate salts (DE 199 59 722 and U.S. Ser. No. 09/732,899, filed Dec. 11, 2000) of the general formulae

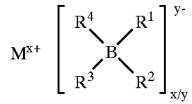

in which:

M is a metal ion or tetraalkylammonium ion, x and y are 1, 2, 3, 4, 5 or 6, $R^1$ to $R^4$ are identical or different and are alkoxy or carboxyl radicals ($C_1$–$C_8$), which are optionally bonded directly to one another by a single or double bond, may also be present. These borate salts are prepared by reacting lithium tetraalkoxyborate or a 1:1 mixture of lithium alkoxide with a borate with a suitable hydroxyl or carboxyl compound in a ratio of 2:1 or 4:1 in an aprotic solvent.

Additives, such as silane compounds of the general formula $$SiR^1R^2R^3R^4$$

where $R^1$ to $R^4$ are H $C_yF_{2y+1-z}H_z$ $OC_yF_{2y+1-z}H_z$ $OC(O)C_yF_{2y+1-z}H_z$ $OSO_2C_yF_{2y+1-z}H_z$ and $1 \leq x \leq 6$ $1 \leq y \leq 8$ and $0 \leq z \leq 2y+1$ and $R^1$–$R^4$ are identical or different and are an aromatic ring from the group consisting of phenyl and naphthyl, which may be unsubstituted or monosubstituted or polysubstituted by F, $C_yF_{2y+1-z}H_z$, $OC_yF_{2y+1-z}H_z$, $OC(O)C_yF_{2y+1-z}H_z$, $OSO_2C_yF_{2y+1-z}H_z$ or $N(C_nF_{2n+1-z}H_z)_2$, or are a heterocyclic aromatic ring from the group consisting of pyridyl, pyrazyl and pyrimidyl, each of which may be monosubstituted or polysubstituted by F, $C_yF_{2y+1-z}H_z$, $OC_yF_{2y+1-z}H_z$, $OC(O)C_yF_{2y+1-z}H_z$, $OSO_2C_yF_{2y+1-z}H_z$ or $N(C_nF_{2n+1-z}H_z)_2$ (DE 100 276 26 and U.S. Ser. No. 09/875,047, filed Jun. 17, 2001), may also be present.

The compounds according to the invention may also be employed in electrolytes comprising lithium fluoroalkylphosphates of the following formula $$Li^+[PF_x(C_yF_{2y+1-z}H_z)_{6-x}]^-$$

in which $1 \leq x \leq 5$ $3 \leq y \leq 8$ $0 \leq z \leq 2y+1$ and the ligands ($C_yF_{2y+1-z}H_z$) may be identical or different, with the exception of the compounds of the general formula $$Li^+[PF_a(CH_bF_c(CF_3)_d)_e]^-$$

in which a is an integer from 2 to 5, b=0 or 1, c=0 or 1, d=2 and e is an integer from 1 to 4, with the provisos that b and c are not simultaneously each=0, and the sum a+e is equal to 6, and the ligands $(CH_bF_c(CF_3)_d)$ may be identical or different (DE 100 089 55 and U.S. Ser. No. 09/572,939, filed May 18, 2000). The process for the preparation of these lithium fluoroalkylphosphates is characterised in that at least one compound of the general formula

| | |
|---|---|
| $H_mP(C_nH_{2n+1})_{3-m}$ | (III), |
| $OP(C_nH_{2n+1})_3$ | (IV), |
| $Cl_mP(C_nH_{2n+1})_{3-m}$ | (V), |
| $F_mP(C_nH_{2n+1})_{3-m}$ | (VI), |
| $Cl_oP(C_nH_{2n+1})_{5-o}$ | (VII), |
| $F_oP(C_nH_{2n+1})_{5-o}$ | (VIII), | in each of which $0 \leq m \leq 2$, $3 \leq n \leq 8$ and $0 \leq o \leq 4$, is fluorinated by electrolysis in hydrogen fluoride, the resultant mixture of fluorination products is separated by extraction, phase separation and/or distillation, the resultant fluorinated alkylphosphorane is reacted with lithium fluoride in an aprotic solvent mixture with exclusion of moisture, and the resultant salt is purified and isolated by conventional methods.

The compounds according to the invention may also be employed in electrolytes which comprise salts of the formula $$Li[P(OR^1)_a(OR^2)_b(OR^3)_c(OR^4)_d F_e]$$

in which $0<a+b+c+d\leq 5$ and $a+b+c+d+e=6$, and $R^1$ to $R^4$, independently of one another, are alkyl, aryl or heteroaryl radicals, where at least two of $R^1$ to $R^4$ may be linked directly to one another via a single or double bond (DE 100 16 801 and U.S. Ser. No. 09/825,868, filed Apr. 15, 2001). The compounds are prepared by reacting phosphorus(V) compounds of the general formula $$P(OR^1)_a(OR^2)_b(OR^3)_c(OR^4)_d F_e$$

in which $0<a+b+c+d\leq 5$ and $a+b+c+d+e=5$, and $R^1$ to $R^4$ are as defined above, with lithium fluoride in the presence of an organic solvent.

It is also possible for ionic liquids of the general formula $$K^+A^-$$

in which:

$K^+$ is a cation selected from the group consisting of

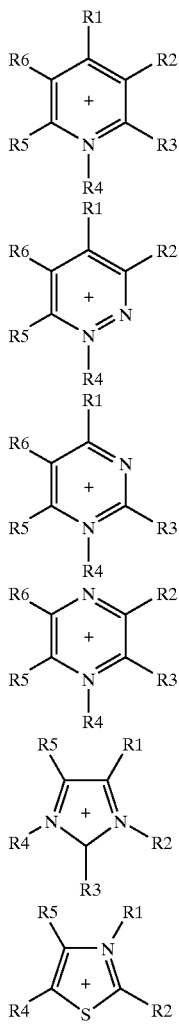

-continued

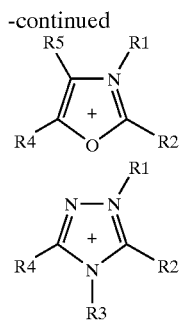

where $R^1$ to $R^5$ are identical or different, are optionally bonded directly to one another by a single or double bond, and each, individually or together, have the following meaning:

H, halogen, an alkyl radical ($C_1$ to $C_8$), which may be partially or fully substituted by further groups, F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x\leq 13$, and $A^-$ is an anion selected from the group consisting of $$[B(OR^1)_n(OR^2)_m(OR^3)_o(OR^4)_p]^-$$

where $0\leq n, m, o, p\leq 4$, and m+n+o+p=4, where $R^1$ to $R^4$ are different or are identical in pairs, are optionally bonded directly to one another by a single or double bond and are each, individually or together, an aromatic ring from the group consisting of phenyl, naphthyl, anthracenyl and phenanthrenyl, which may be unsubstituted or monosubstituted or polysubstituted by $CnF_{(2n+1-x)}H_x$, where $1<n<6$ and $0<x\leq 13$, or halogen (F, Cl or Br), an aromatic heterocyclic ring from the group consisting of pyridyl, pyrazyl and pyrimidyl, which may be unsubstituted or monosubstituted or polysubstituted by $C_nF_{(2n+1-x)}H_x$, where $1<n<6$ and $0<x\leq 13$, or halogen (F, Cl or Br), an alkyl radical ($C_1$ to $C_8$), which may be partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x\leq 13$, or $OR^1$ to $OR^4$ individually or together are an aromatic or aliphatic carboxyl, dicarboxyl, oxysulfonyl or oxycarbonyl radical, which may be partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x\leq 13$ (DE 100 265 65 and U.S. Ser. No. 09/866,926 filed May 30, 2001), to be present in the electrolyte.

It is also possible for ionic liquids $K^+A^-$ where $K^+$ is as defined above and $A^-$ is an anion selected from the group consisting of $$[PF_x(C_yF_{2y+1-z}H_z)_{6-x}]^-$$

and $1\leq x<6$ $1\leq y\leq 8$ and $0\leq z\leq 2y+1$ to be present (DE 100 279 95 and U.S. Ser. No. 09/877,259, filed Jun. 11, 2001).

The compounds according to the invention may also be present in electrolytes comprising compounds of the following formula:

$$NR^1R^2R^3$$

in which
R$^1$ and R$^2$ are H, C$_y$F$_{2y+1-z}$H$_z$ or (C$_n$F$_{2n-m}$H$_m$)X, where X is an aromatic or heterocyclic radical, and
R$^3$ is (C$_n$F$_{2n-m}$H$_m$)Y, where Y is a heterocyclic radical, or (C$_o$F$_{2o-p}$H$_p$)Z, where Z is an aromatic radical,
and where n, m, o, p, y and z satisfy the following conditions:
$0 \leq n \leq 6$,
$0 \leq m \leq 2n$,
$2 \leq o \leq 6$,
$0 \leq p \leq 2o$,
$1 \leq y \leq 8$, and
$0 \leq z \leq 2y+1$,
for reducing the acid content in aprotic electrolyte systems in electrochemical cells.

It is also possible for fluoroalkylphosphates of the general formula $$M^{n+}[PF_x(C_yF_{2y+1-z}H_z)_{6-x}]_n^-$$

in which
$1 \leq x \leq 6$
$1 \leq y \leq 8$
$0 \leq z \leq 2y+1$
$1 \leq n \leq 3$ and
M$^{n+}$ is a monovalent to trivalent cation, in particular:
NR$^1$R$^2$R$^3$R$^4$,
PR$^1$R$^2$R$^3$R$^4$,
P[(NR$^1$R$^2$)$_k$R$^3_m$R$^4_{4-k-m}$]
(where k=1–4, m=0–3 and k+m≦4),
C(NR$^1$R$^2$)(NR$^3$R$^4$)(NR$^5$R$^6$),
C(aryl)$_3$, Rb or tropylium,
where R$^1$ to R$^8$ are H, alkyl or aryl (C$_1$–C$_8$), which may be partially substituted by F, Cl or Br,
with the exception of M$^{n+}$=Li$^+$, Na$^+$, Cs$^+$, K$^+$ and Ag$^+$. These fluoroalkyl-phosphates are obtainable by reacting phosphoranes with a fluoride or metal fluoroalkylphosphates with a fluoride or chloride in organic aprotic solvents (DE 100 388 58 and U.S. Ser. No. 09/918,464, filed August, 2001).

The electrolyte may also comprise a mixture that comprises
a) at least one lithium fluoroalkylphosphate salt of the general formula $$Li^+[PF_x(C_yF_{2y+1-z}H_z)_{6-x}]^-$$

in which
$1 \leq x \leq 5$
$1 \leq y \leq 8$, and
$0 \leq z \leq 2y+1$
and the ligands (C$_y$F$_{2y+1-z}$H$_z$) are in each case identical or different, and
b) at least one polymer (DE 100 58 264).

The electrolyte may also comprise tetrakisfluoroalkyl borate salts of the general formula $$M^{n+}([BR_4]^-)_n$$

in which
M$^{n+}$ is a monovalent, divalent or trivalent cation,
the ligands R are in each case identical and are (C$_x$F$_{2x+1}$), where $1 \leq x \leq 8$, and n=1, 2 or 3 (DE 100 558 11). The process for the preparation of tetrakisfluoroalkyl borate salts is characterised in that at least one compound of the general formula M$^{n+}$ ([B(CN)$_4$]$^-$)$_n$, in which M$^{n+}$ and n are as defined above, is fluorinated by reaction with at least one fluorinating agent in at least one solvent, and the resultant fluorinated compound is purified and isolated by conventional methods.

The electrolyte may also comprise borate salts of the general formula $$M^{n+}[BF_x(C_yF_{2y+1-z}H_z)_{4-x}]_n^-$$

in which:
$1<x<3$, $1 \leq y \leq 8$ and $0 \leq z \leq 2y+1$, and
M is a monovalent to trivalent cation ($1 \leq n \leq 3$), apart from potassium and barium,
in particular:
Li,
NR$^1$R$^2$R$^3$R$^4$, PR$^5$R$^6$R$^7$R$^8$, P(NR$^5$R$^6$)$_k$R$^7_m$R$^8_{4-k-m}$ (where k=1–4, m=0–3 and k+m≦4), or
C(NR$^5$R$^6$)(NR$^7$R$^8$)(NR$^9$R$^{10}$), where
R$^1$ to R$^4$ are C$_y$F$_{2y+1-z}$H$_z$ and
R$^5$ to R$^{10}$ are H or C$_y$F$_{2y+1-z}$H$_z$, or
an aromatic heterocyclic cation, in particular a nitrogen- and/or oxygen- and/or sulfur-containing aromatic heterocyclic cation (DE 101 031 89 and U.S. Ser. No. 10/050, 151, filed Jan. 18, 2002). The process for the preparation of these compounds is characterised in that
a) BF$_3$/solvent complexes are reacted 1:1 with alkyllithium with cooling, the majority of the solvent is removed after slow warming, and the solid is subsequently filtered off and washed with a suitable solvent, or
b) lithium salts in a suitable solvent are reacted 1:1 with B(CF$_3$)F$_3$ salts, the mixture is stirred at elevated temperature, the solvent is removed, aprotic non-aqueous solvents, preferably solvents which are used in electrochemical cells, are added to the reaction mixture, and the mixture is dried, or
c) B(CF$_3$)F$_3$ salts are reacted 1:1 to 1:1.5 with lithium salts in water at elevated temperature and heated at the boiling point for from 0.5 to 2 hours, the water is removed, aprotic non-aqueous solvents, preferably solvents which are used in electrochemical cells, are added to the reaction mixture and the mixture is dried.

The electrolyte may also comprise fluoroalkylphosphate salts of the general formula $$M^{n+}([PF_x(C_yF_{2y+1-z}H_z)_{6-x}]^-)_n$$

in which
M$^{n+}$ is a monovalent, divalent or trivalent cation,
$1 \leq x \leq 5$,
$1 \leq y \leq 8$ and
$0 \leq z \leq 2y+1$, n=1, 2 or 3, and the ligands (C$_y$F$_{2y+1-z}$H$_z$) are in each case identical or different, where the fluoroalkylphosphate salts in which M$^{n+}$ is a lithium cation and the salts
M$^+$([PF$_4$(CF$_3$)$_2$]$^-$) where M$^+$=Cs$^+$, Ag$^+$ or K$^+$,
M$^+$([PF$_4$(C$_2$F$_5$)$_2$]$^-$) where M$^+$=Cs$^+$,
M$^+$([PF$_3$(C$_2$F$_5$)$_3$]$^-$) where M$^+$=Cs$^+$, K$^+$, Na$^+$ or para-Cl(C$_6$H$_4$)N$_2^+$,
M$^+$([PF$_3$(C$_3$F$_7$)$_3$]$^-$) where M$^+$=Cs$^+$, K$^+$, Na$^+$, para-Cl(C$_6$H$_4$)N$_2^+$ or
para-O$_2$N(C$_6$H$_4$)N$_2^+$, are excluded (DE 100 558 12). The process for the preparation of these fluoroalkylphosphate salts is characterised in that at least one compound of the general formula $H_rP(C_sH_{2s+1})_{3-r}$, $OP(C_sH_{2s+1})_3$, $Cl_rP(C_sH_{2s+1})_{3-r}$, $F_rP(C_sH_{2s+1})_{3-r}$, $Cl_tP(C_sH_{2s+1})_{5-t}$ and/or $F_tP(C_sH_{2s+1})_{5-t}$, in which in each case
$0 \leq r \leq 2$
$3 \leq s \leq 8$ and
$0 \leq t \leq 4$, is fluorinated by electrolysis in hydrogen fluoride, the resultant mixture of fluorination products is separated, and the resultant fluorinated alkylphosphorane is reacted with a compound of the general formula $M^{n+}(F^-)_n$, in which $M^{n+}$ and n are as defined above, in an aprotic solvent or solvent mixture with exclusion of moisture, and the resultant fluoroalkylphosphate salt is purified and isolated by conventional methods.

The compounds according to the invention can be used in electrolytes for electrochemical cells containing positive-electrode material consisting of coated metal cores selected from the group consisting of Sb, Bi, Cd, In, Pb, Ga and tin or alloys thereof (DE 100 16 024 and U.S. Ser. No. 09/821,683, filed Mar. 30, 2001). The process for the preparation of this positive-electrode material is characterised in that
 a) a suspension or sol of the metal or alloy core in urotropin is prepared,
 b) the suspension is emulsified with $C_5$–$C_{12}$-hydrocarbons,
 c) the emulsion is precipitated onto the metal or alloy cores, and
 d) the metal hydroxides or oxyhydroxides are converted into the corresponding oxide by heating the system.

The compounds according to the invention can also be employed in electrolytes for electrochemical cells having negative electrodes made from common lithium intercalation and insertion compounds, but also with negative-electrode materials consisting of lithium mixed oxide particles coated with one or more metal oxides (DE 199 22 522 and U.S. Ser. No. 09/959,983, filed Nov. 14, 2001). They may also consist of lithium mixed oxide particles which are coated with one or more polymers (DE 199 46 066 and U.S. Ser. No. 09/668,282, filed Sep. 25, 2000), obtained by a process in which the particles are suspended in a solvent, and the coated particles are subsequently filtered off, dried and optionally calcined. The compounds according to the invention may likewise be employed in systems having negative electrodes consisting of lithium mixed oxide particles with one or more coatings of alkali metal compounds and metal oxides (DE100 14 884 and U.S. Ser. No. 09/816,663, filed Mar. 26, 2001). The process for the production of these materials is characterised in that the particles are suspended in an organic solvent, an alkali metal salt compound suspended in an organic solvent is added, metal oxides dissolved in an organic solvent are added, a hydrolysis solution is added to the suspension, and the coated particles are subsequently filtered off, dried and calcined. The compounds according to the invention can likewise be employed in systems comprising positive-electrode materials with doped tin oxide (DE 100 257 61 and U.S. Ser. No. 09/864,874, filed Mar. 25, 2001). This positive-electrode material is prepared by
 a) adding urea to a tin chloride solution,
 b) adding urotropin and a suitable doping compound to the solution,
 c) emulsifying the resultant sol in petroleum ether,
 d) washing the resultant gel and removing the solvent by suction, and
 e) drying and heating the gel.

The compounds according to the invention can likewise be employed in systems comprising positive-electrode materials with reduced tin oxide (DE 100 257 62 and U.S. Ser. No. 09/864,092, filed May 24, 2001). This positive-electrode material is prepared by
 a) adding urea to a tin chloride solution,
 b) adding urotropin to the solution,
 c) emulsifying the resultant sol in petroleum ether,
 d) washing the resultant gel and removing the solvent by suction,
 e) drying and heating the gel, and
 f) exposing the resultant $SnO_2$ to a reducing gas stream in an aeratable oven.

The entire disclosure of all applications, patents and publications, cited above and below and of corresponding German Application No. 10109032.3, filed Feb. 24, 2001 is hereby incorporated by reference.

In the foregoing and in the following examples, all temperatures are set forth uncorrected in degrees Celsius; and unless otherwise indicated, all parts and percentages are by weight.

The invention is explained below with relevance to examples. These examples serve merely to explain the invention and do not restrict the general inventive concept.

EXAMPLES

Example 1

Synthesis of dilithium perfluoro-1,2-bis(diethyltrifluorophosphato)ethane 9.50 g of a solvent mixture (ethylene carbonate:dimethyl carbonate:diethylcarbonate=2:2:1 ratio by weight) and 3.50 g (4.9 mmol) of perfluoro-1,2-bis(diethyldifluorophosphorano)ethane were added at room temperature to 0.44 g (16.9 mmol) of LiF in a PFA vessel under a dry gas atmosphere. The reaction mixture was stirred at room temperature for three hours until all the perfluoro-1,2-bis(diethyldifluorophosphorano)ethane (base sediment) had dissolved. The excess LiF was filtered off, and the solution (electrolyte), which comprised 3.75 g of dilithium perfluoro-1,2-bis(diethyltrifluorophosphato)ethane (corresponding to a salt concentration in the electrolyte solution of 28.3% or 0.48 mol/l), was analysed by $^{19}F$ and $^{31}P$ NMR spectra. To this end, the spectra were measured for clean electrolytes in an FEP tube without dilution with another solvent using a special method ($CD_3COCD_3$ film). $CCl_3F$ was used as external reference in the film. The frequency of 566.22 Hz of 85% $H_3PO_4$ in water as $^{31}P$ reference in acetone-$D_6$ was separately determined experimentally. Both $^{19}F$ and $^{31}P$ NMR spectra were measured using a Bruker DRX 500 spectrometer (470.6 MHz for $^{19}F$ and 202.5 MHz for $^{31}P$).

The $^{19}F$ and $^{31}P$ NMR spectra show the formation of different stereoisomers of the salt dilithium perfluoro-1,2-bis(diethyltrifluorophosphato)ethane through the reaction of the fluoride ion with the phosphorus atom between perfluoroethyl groups or between perfluoroethyl group and perfluoroethylene bridge in the starting molecule per fluoro-1,2-bis(diethyldifluorophosphorano)ethane.

$2Li^+[(C_2F_5)_2PF_3(CF_2)_2PF_3(C_2F_5)_2]^{2-}$

Isomer A (About 67%)

$^{19}$F NMR: −46.19 dm (2 F, 2 PF); −87.57 dm (4 F, 2 PF$_2$); −82.28 m (6 F, 2 CF$_3$); −82.42 m (6 F, 2 CF$_3$); −112.00 dm (4 F, 2 CF$_2$); −115.13 dm (4 F, 2 CF$_2$); −116.25 dm (4 F, 2 CF$_2$); $J^1_{P,F}$=927 Hz; $J^1_{P,F}$=922 Hz; $J^2_{P,F}$=105 Hz; $J^2_{P,F}$=74 Hz; $J^2_{P,F}$=77 Hz. $^{31}$P NMR: −144.7 qm

Isomer B (About 33%)

$^{19}$F NMR: −43.39 dm (2 F, 2 PF); −87.73 dm (4 F, 2 PF$_2$); −80.39 m (12 F, 4 CF$_3$); −110.55 dm (4 F, 2 CF$_2$); −115.70 dm (8 F, 4 CF$_2$); $J^1_{P,F}$=860 Hz; $J^1_{P,F}$=930 Hz. $^{31}$P NMR: −144.8 qm

Example 2

Synthesis of a Mixture of Dilithium perfluoro-1,2-bis(diethyltrifluorophosphato)-ethane and lithium tris(pentafluoroethyl)trifluorophosphate 9.27 g of a solvent mixture (ethylene carbonate: dimethyl carbonate:diethyl carbonate=2:2:1 ratio by weight) and 3.39 g of a mixture of perfluoro-1,2-bis(diethyldifluorophosphorano)ethane (about 60 mol %) and tris(pentafluoroethyl)difluorophosphorane (about 40 mol %) [this mixture was prepared by electrochemical fluorination of 1,2-bis(diethylphosphino)ethane and used further without separation] were added at room temperature to 0.46 g (17.7 mmol) of LiF in a PFA vessel under a dry gas atmosphere. The reaction mixture was stirred at room temperature for three hours until all the perfluorinated starting material (base sediment) had dissolved. The excess LiF was filtered off, and the solution (electrolyte), which comprised 2.6 g of dilithium perfluoro-1,2-bis(diethyltrifluorophosphato)ethane (corresponding to a salt concentration in the electrolyte solution of 0.34 mol/l) and 1.02 g of lithium tris(pentafluoroethyl)trifluorophosphate (corresponding to a salt concentration in the electrolyte solution of 0.23 ml/l), was analysed by $^{19}$F and $^{31}$P NMR spectra. The total concentration of the salt in the electrolyte solution was 28.1%. To this end, the spectra were measured as described under Example 1 and confirm the presence of the two salts in the solution.

$2Li^+[(C_2F_5)_2PF_3(CF_2)_2PF_3(C_2F_5)_2]^{-2}$ (about 60 mol %)

$^{31}$P NMR: −144.7 qm $Li^+[(C_2F_5)_3PF_3]^-$ $^{31}$P NMR: −150.3 qm

Example 3

Synthesis of di(tetraethylammonium)perfluoro-1,2-bis(diethyltrifluorophosphato)ethane The synthesis of di(tetraethylammonium)perfluoro-1,2-bis(diethyltrifluorophosphato)ethane was carried out analogously to the synthesis described in Example 1, with anhydrous tetraethylammonium fluoride being used instead of LiF.

$^{19}$F and $^{31}$P NMR analyses show exclusively signals which can be assigned to the anion (see Example 1).

Example 4

Oxidation Stability of the perfluoro-1,2-bis(diethyltrifluorophosphato)ethane Anion In a measurement cell with platinum working electrode, lithium counter-electrode and lithium reference electrode, in each case 5 cyclic voltammograms were recorded one after the other. To this end, the potential was firstly increased starting from the rest potential at a rate of 10 mV/s to 6 V against Li/Li+, and then moved back to the rest potential.

Electrolyte: 0.5 mol/kg$_{solvent}$ (molality) of dilithium perfluoro-1,2-bis(diethyltrifluorophosphato)ethane in EC/DMC (1:1, ethylene carbonate/-dimethyl carbonate). The oxidation potential was determined as >5 V against Li/Li$^+$ (in this respect, see FIG. 1).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A fluoroalkylphosphate salt of formula (I)

$$(M^{a+})_b[(C_nF_{2n+1-m}H_m)_yPF_{5-y}(CR_1R_2)_xPF_{5-y}(C_nF_{2n+1-m}H_m)_y]^{(2-)}{}_{(a \cdot b/2)} \quad (I)$$

wherein
M$^{a+}$ is a monovalent, divalent or trivalent cation selected from lithium, sodium, magnesium, aluminum, nitrosyl, nitryl or organic cations;

a is 1, 2 or 3;

b is 2 for a=1, b is 2 for a=3, and b is 1 for a=2;

and, in each case, subscripts n, m, x and y satisfy the following relationships $1 \leq n \leq 8$, $0 \leq m \leq 2$ for n=1 or 2, $0 \leq m \leq 4$ for $3 \leq n \leq 8$, $1 \leq x \leq 12$, $0 \leq y \leq 2$, where R$_1$ and R$_2$ are each independently, fluorine, hydrogen, alkyl having 1 to 8 carbon atoms, fluoroalkyl having 1 to 8 carbon atoms or perfluoroalkyl having 1 to 8 carbon atoms; and wherein the substituents (C$_n$F$_{2n+1-m}$H$_m$) are in each case identical or different.

2. A fluoroalkylphosphate salt according to claim 1, wherein said salt is $(Li^+)_2[(C_2F_5)_2PF_3(CF_2)_2PF_3(C_2F_5)_2]^{(2-)}$ or $(N(C_2H_5)_4{}^+)_2[(C_2F_5)_2PF_3(CF_2)_2PF_3(C_2F_5)_2]^{(2-)}$.

3. A fluoroalkyphosphate salt according to claim 1, wherein cation M$^{a+}$ is a lithium or sodium cation.

4. A fluoroalkylphosphate salt according to claim 3, wherein the cation M$^{a+}$ is a lithium cation.

5. A fluoroalkylphosphate salt according to claim 1, wherein the cation M$^{a+}$ is a magnesium or aluminum cation.

6. A fluoroalkylphosphate salt according to claim 1, wherein the cation M$^{a+}$ is an organic cation.

7. A fluoroalkylphosphate salt according to claim 1, wherein the cation M$^{a+}$ is a nitrosyl cation, a nitryl cation or an organic cation selected from the formulae $[N(R^7)_4]^+$, $[P(R^7)_4]^+$, $[P(N(R^7)_2)_4]^+$ or $[C(N(R^7)_2)_3]^+$, wherein
R$^7$, in each case independently, is H, C$_{1-10}$- alkyl or A, where one or more H atoms in the C$_{1-10}$-alkyl chain may each individually be replaced by fluorine, an aromatic radical which optionally contains one or more heteroatoms, or a cycloalkyl radical which optionally contains one or more heteroatoms, and/or one or more C atoms in the alkyl chain may be each individually replaced by a heteroatom, and A is an aromatic or cycloaliphatic radical, in each case optionally containing one or more heteroatoms.

8. A fluoroalkylphosphate salt according to claim 7, wherein A is in each case a 5- or 6-membered aromatic radical which optionally contains nitrogen, sulfur and/or oxygen atoms, or a cycloalkyl radical having 5 or 6 members.

9. A fluoroalkylphosphate salt according to claim 8, wherein A is phenyl or pyridyl.

10. A fluoroalkylphosphate salt according to claim 1, wherein the $M^{a+}$ is a nitrosyl cation, a nitryl cation or an organic cation selected from the formulae $$[N(R^7)_4]^+, [P(R^7)_4]^+, [P(N(R^7)_2)_4]^+ \text{ or } [C(N(R^7)_2)_3]^+,$$

wherein $R^7$ are in each case, independently, H, $C_{1-10}$- alkyl or A, where one or more H atoms in the $C_{1-10}$-alkyl chain may each individually be replaced by fluorine, a 5- or 6-membered aromatic radical which optionally contains one or more heteroatoms selected from N, O and S, or a 5- or 6-numbered cycloalkyl radical which optionally contains one or more heteroatoms selected from N, O and S, and/or one or more C atoms in the $C_{1-10}$-alkyll chain may be each individually replaced by oxygen, and A is an aromatic or cycloaliphatic radical, in each case optionally containing one or more heteroatoms.

11. A fluoroalkylphosphate salt according to claim 1, wherein $M^{a+}$ is a heteroaromatic cation of formulae (II) to (IX)

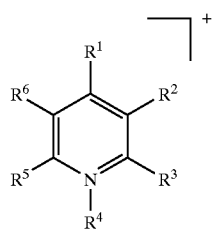
(II)

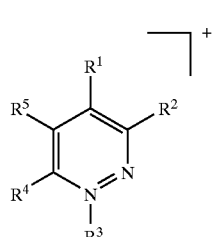
(III)

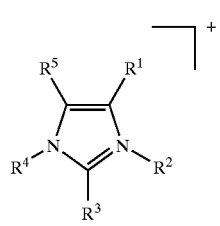
(VI)

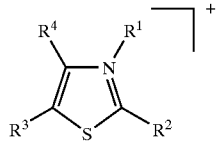
(VII)

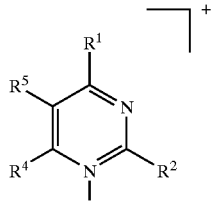
(IV)

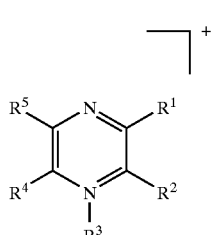
(V)

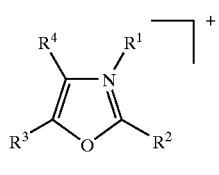
(VIII)

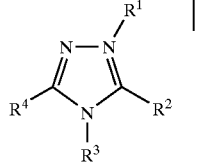
(IX)

wherein $R^1$ to $R^6$ are each independently, H, halogen, or a $C_{1-8}$-alkyl radical which is optionally substituted by F, Cl, $N(C_rF_{(2r+1-s)}H_s)_2$, $O(C_rF_{(2r+1-s)}H_s)$, $SO_2(C_rF_{(2r+1-s)}H_s)$ or $C_rF_{(2r+1-s)}H_s$, in which $1 \leq r \leq 6$ and $0 \leq s \leq 13$, and $2r+1-s \leq 0$, or one or more adjacent pairs of $R^1$ to $R^6$ can together be a $C_{1-8}$-alkylene radical which is optionally substituted by F, Cl, $N(C_rF_{(2r+1-s)}H_s)_2$, $O(C_rF_{(2r+1-s)}H_s)$, $SO_2(C_rF_{(2r+1-s)}H_s)$ or $C_rF_{(2r+1-s)}H_s$, in which $1 \leq r \leq 6$ and $0 \leq s \leq 13$, and $2r+1-s \leq 0$, where each of $R^1$ to $R^6$ cannot be halogens if they are bonded directly to nitrogen.

12. A fluoroalkylphosphate salt according to claim 11, wherein $R^1$ to $R^6$ are each independently H, fluorine, or a $C_{1-8}$-alkyl radical which is optionally substituted by F, Cl, $N(C_rF_{(2r+1-s)}H_s)_2$, $O(C_rF_{(2r+1-s)}H_s)$, $SO_2(C_rF_{(2r+1-s)}H_s)$ or $C_rF_{(2r+1-s)}H_s$, in which $1 \leq r \leq 6$ or $0 \leq s \leq 2r+1$, and $2r+1-s \leq 0$, and where each of $R^1$ to $R^6$ cannot be fluorine if they are bonded directly to nitrogen.

13. A fluoroalkylphosphate salt according to claim 1, wherein $1 \leq n \leq 6$.

14. A fluoroalkylphosphate salt according to claim 13, wherein $1 \leq n \leq 3$.

15. A fluoroalkylphosphate salt according to claim 1, wherein $1 \leq x \leq 8$.

16. A fluoroalkylphosphate salt according to claim 15, wherein $1 \leq x \leq 4$.

17. A fluoroalkylphosphate salt according to claim 1, wherein m=0.

18. A fluoroalkylphosphate salt according to claim 1, wherein y=2.

19. A fluoroalkylphosphate salt according to claim 1, wherein $R_1$ and $R_2$ are each fluorine.

20. A process for the preparation of a fluoroalkylphosphate salt according to claim 1, comprising:

reacting at least one fluoro-α,ω-bis[(fluoroalkyl)fluorophosphorano]alkane with at least one fluoride salt of the formula (X)

$$(M^{a+})[F^-]_a \quad (X)$$

in which ($M^{a+}$) and a are as defined in claim 1, in solution to obtain a fluoroalkylphosphate salt of the formula (I), and said salt is optionally, purified and/or isolated.

21. A process according to one of claim 20, wherein that the solvent employed is ethylene carbonate, propylene carbonate, butylene carbonate, dimethyl carbonate, diethyl carbonate, ethyl methyl carbonate, methyl propyl carbonate, methyl formate, ethyl formate, methyl acetate, ethyl acetate, methyl propionate, ethyl propionate, methyl butyrate, ethyl butyrate, γ-butyrolactone, diethyl ether, dimethoxyethane, diethoxyethane, dimethylformamide or dimethylacetamide, dimethyl sulfoxide, dimethyl sulfide, diethyl sulfide propane sulfone acetonitrile, acrylonitrile, propionitrile, acetone, or at least partially fluorinated ethylene carbonate, propylene carbonate, butylene carbonate, dimethyl carbonate, diethyl carbonate, ethyl methyl carbonate, methyl propyl carbonate, methyl formate, ethyl formate, methyl acetate, ethyl acetate, methyl propionate, ethyl propionate, methyl butyrate, ethyl butyrate, γ-butyrolactone, diethyl ether, dimethoxyethane, diethoxyethane, dimethylformamide or dimethylacetamide, dimethyl sulfoxide dimethyl sulfide diethyl sulfide propane sulfone acetonitrile, acrylonitrile, propionitrile, acetone, or a mixture of at least two of these solvents.

22. A process according to claim 20, wherein said at least one fluoro-α,ω-bis[(fluoroalkyl)fluorophosphorano]alkane is a compound of formula (XI)

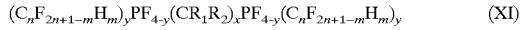

$$(C_nF_{2n+1-m}H_m)_yPF_{4-y}(CR_1R_2)_xPF_{4-y}(C_nF_{2n+1-m}H_m)_y \quad (XI)$$

in which $1 \leq n \leq 8$, $0 \leq m \leq 2$ for n=1 or 2, $0 \leq m \leq 4$ for $3 \leq n \leq 8$, $1 \leq x \leq 12$, $0 \leq y \leq 2$, $R_1$ and $R_2$ are each, independently, fluorine, hydrogen, alkyl having 1 to 8 C atoms, fluoroalkyl having 1 to 8 C atoms or perfluoroalkyl having 1 to 8 C atoms, and substituents $(C_nF_{2n+1-m}H_m)$ are in each case identical or different.

23. A process according to claim 20, wherein the compound of the formula (X) is employed in an excess of up to 10 fold, based on the amount of fluoro-α,ω-bis[(fluoroalkyl)fluorophosphorano]alkane(s).

24. A process according to one of claim 20, wherein the reaction with the compound of formula (X) is carried out at a temperature of −35 to +80° C.

25. A mixture comprising:

a) at least one fluoroalkylphosphate salt according to claim 1, and b) at least one polymer.

26. A mixture according to claim 25, wherein said at least one polymer is at least partially crosslinked.

27. A mixture according to claim 25, comprising 5 to 90% by weight of a) and 95 to 5% by weight of component b), based on the sum of a) and b).

28. A mixture according to claim 25, wherein b) is a homopolymer or copolymer of acrylonitrile, vinylidene difluoride, methyl methacrylate, tetrahydrofuran, ethylene oxide, siloxane, phosphazene or a mixture of at least two of these homopolymers and/or copolymers.

29. A mixture according to claim 28, wherein b) is a homopolymer or copolymer of vinylidene difluoride, acrylonitrile, methyl methacrylate or tetrahydrofuran.

30. A mixture according to claim 25, wherein said mixture additionally comprises at least one solvent.

31. A mixture according to claim 30, wherein said solvent is ethylene carbonate, propylene carbonate, butylene carbonate, dimethyl carbonate, diethyl carbonate, ethyl methyl carbonate, methyl propyl carbonate, methyl formate, ethyl formate, methyl acetate, ethyl acetate, methyl propionate, ethyl propionate, methyl butyrate, ethyl butyrate, γ-butyrolactone, diethyl ether, dimethoxyethane, diethoxyethane, dimethylformamide, dimethylacetamide, dimethyl sulfoxide, dimethyl sulfide, diethyl sulfide or propane sulfone, acetonitrile, acrylonitrile, acetone, or at least partially fluorinated ethylene carbonate, propylene carbonate, butylene carbonate, dimethyl carbonate, diethyl carbonate, ethyl methyl carbonate, methyl propyl carbonate, methyl formate, ethyl formate, methyl acetate, ethyl acetate, methyl propionate, ethyl propionate, methyl butyrate, ethyl butyrate, γ-butyrolactone, diethyl ether, dimethoxyethane, diethoxyethane, dimethylformamide, dimethylacetamide, dimethyl sulfoxide, dimethyl sulfide, diethyl sulfide or propane sulfone, acetonitrile, acrylonitrile, acetone, or a mixture of at least two of these solvents.

32. In an electrolyte, primary battery, secondary battery, capacitor, supercapacitor or galvanic cell, which in each contains at least one conductive salt, the improvement wherein, in each case, said salt is a salt according to claim 1.

33. A galvanic cell according to claim 32.

34. An electrolyte according to claim 32.

35. An electrolyte according to claim 34, wherein the concentration of the fluoroalkylphosphate salt is 0.01 to 3 mol/l.

36. A primary battery according to claim 32.

37. A secondary battery according to claim 32.

38. A capacitor according to claim 32.

39. A supercapacitor according to claim 32.

40. A fluoroalkylphosphate salt of formula (I)

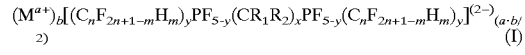

$$(M^{a+})_b[(C_nF_{2n+1-m}H_m)_yPF_{5-y}(CR_1R_2)_xPF_{5-y}(C_nF_{2n+1-m}H_m)_y]^{(2-)}_{(a \cdot b/2)} \quad (I)$$

wherein $M^{a+}$ is a monovalent, divalent or trivalent cation;

a is 1,2 or 3;

b is 2 for a=1, b is 2 for a=3, and b is 1 for a=2;

and, in each case, subscripts n, m, x and y satisfy the following relationships $1 \leq n \leq 8$, $0 \leq m \leq 2$ for $n=1$ or $2$,
$0 \leq m \leq 4$ for $3 \leq n \leq 8$,
$1 \leq x \leq 12$,
$0 \leq y \leq 2$,
where $R_1$ and $R_2$ are each independently, fluorine, hydrogen, alkyl having 1 to 8 carbon atoms, fluoroalkyl having 1 to 8 carbon atoms or perfluoroalkyl having 1 to 8 carbon atoms; and wherein the substituents $(C_nF_{2n+1-m}H_m)$ are in each case identical or different.

41. A fluoroalkylphosphate salt of formula (I)

(I)

wherein
$M^{a+}$ is a monovalent, divalent or trivalent cation;
a is 1,2 or 3;
b is 2 for a=1,
b is2 for a=3, and
b is 1 for a=2;
and, in each case, subscripts n, m, x and y satisfy the following relationships
$1 \leq n \leq 8$,
$0 \leq m \leq 2$ for $n=1$ or $2$,
$0 \leq m \leq 4$ for $3 \leq n \leq 8$,
$1 \leq x \leq 12$,
$y=2$,
where $R_1$ and $R_2$ are each independently, fluorine, hydrogen, alkyl having 1 to 8 carbon atoms, fluoroalkyl having 1 to 8 carbon atoms or perfluoroalkyl having 1 to 8 carbon atoms; and
wherein the substituents $(C_nF_{2n+1-m}H_m)$ are in each case identical or different.

42. A fluoroalkylphosphate salt of formula (I)

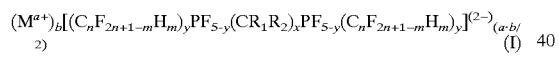
(I)

wherein
$M^{a+}$ is a monovalent, divalent or trivalent cation;
a is 1,2 or 3;
b is 2 for a=1,
b is2 for a=3, and
b is 1 for a=2;
and, in each case, subscripts n, m, x and y satisfy the following relationships
$1 \leq n \leq 8$,
$0 \leq m \leq 2$ for $n=1$ or $2$,
$0 \leq m \leq 4$ for $3 \leq n \leq 8$,
$1 \leq x \leq 12$,
$0 \leq y \leq 2$,
wherein $R_1$ and $R_2$ are each fluorine; and
wherein the substituents $(C_nF_{2n+1-m}H_m)$ are in each case identical or different.

43. A fluoroalkylphosphate salt of formula (I)

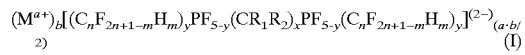
(I)

wherein
$M^{a+}$ is a monovalent, divalent or trivalent cation;
a is 1,2 or 3;
b is 2 for a=1,
b is2 for a=3, and
b is 1 for a=2;
and, in each case, subscripts n, m, x and y satisfy the following relationships
$1 \leq n \leq 8$,
$0 \leq m \leq 2$ for $n=1$ or $2$,
$0 \leq m \leq 4$ for $3 \leq n \leq 8$,
$1 \leq x \leq 12$,
$0 \leq y \leq 2$,
where $R_1$ and $R_2$ are each independently, fluorine, hydrogen, alkyl having 1 to 8 carbon atoms, fluoroalkyl having 1 to 8 carbon atoms or perfluoroalkyl having 1 to 8 carbon atoms; and
wherein the substituents $(C_nF_{2n+1-m}H_m)$ are in each case identical or different.

44. A fluoroalkylphosphate salt of formula (I)

(I)

wherein
$M^{a+}$ is a monovalent, divalent or trivalent cation;
a is 1,2 or 3;
b is 2 for a=1,
b is2 for a=3, and
b is 1 for a=2;
and, in each case, subscripts n, m, x and y satisfy the following relationships
$1 \leq n \leq 8$,
$0 \leq m \leq 2$ for $n=1$ or $2$,
$0 \leq m \leq 4$ for $3 \leq n \leq 8$,
$1 \leq x \leq 12$,
$0 \leq y \leq 2$,
where $R_1$ and $R_2$ are each independently, fluorine, hydrogen, alkyl having 1 to 8 carbon atoms, fluoroalkyl having 1 to 8 carbon atoms or perfluoroalkyl having 1 to 8 carbon atoms; and
wherein the substituents $(C_nF_{2n+1-m}H_m)$ are in each case identical or different.

\* \* \* \* \*

UNITED STATES PATENT AND TRADEMARK OFFICE
CERTIFICATE OF CORRECTION

PATENT NO. : 6,893,774 B2
DATED : May 17, 2005
INVENTOR(S) : Schmidt et al.

It is certified that error appears in the above-identified patent and that said Letters Patent is hereby corrected as shown below:

Column 18,
Line 51, "fluoroalkyphosphate" and insert -- fluoroalkylphosphate --.

Column 21,
Line 19, after "to", delete "one of".
Line 29, after "sulfide", insert -- , --.
Line 30, after "propionitrile," insert -- or --.
Line 39, after "sulfoxide" insert -- , --.
Line 40, after "fide" insert -- , --.
Line 40, after "sulfide" insert -- , --.
Line 40, after ""sulfone" insert -- , --.
Line 41, after "propionitrile," insert -- or --.
Line 61, after "to" delete "one of".

Column 22,
Line 33, delete "γ-butvrolactone" and insert -- γ-butyrolactone --.
Line 42, before "contains" insert -- case --.
Line 61, delete "1,2" and insert -- 1, 2 --.
Line 63, delete "is2" and insert -- is 2 --.

Column 23,
Line 5, delete "hydrogen".
Line 19, delete "1,2" and insert -- 1, 2 --.
Line 21, delete "is2" and insert -- is 2 --.

UNITED STATES PATENT AND TRADEMARK OFFICE
CERTIFICATE OF CORRECTION

PATENT NO. : 6,893,774 B2
DATED : May 17, 2005
INVENTOR(S) : Schmidt et al.

It is certified that error appears in the above-identified patent and that said Letters Patent is hereby corrected as shown below:

Column 24,
Lines 11 and 36, delete "1,2" and insert -- 1, 2 --.
Lines 13 and 38, delete "is2" and insert -- is 2 --.
Line 21, delete "$1 \leqq x \leqq 12$," and insert -- $2 \leq x \leq 12$ --.

Signed and Sealed this

Fourth Day of October, 2005

JON W. DUDAS
*Director of the United States Patent and Trademark Office*